United States Patent
Yu et al.

(10) Patent No.: US 10,610,151 B2
(45) Date of Patent: Apr. 7, 2020

(54) METHOD FOR MEASURING LEVEL OF MUSCLE RELAXATION, PROCESSING DEVICE THEREOF AND INSTRUMENT FOR MEASURING MUSCLE RELAXATION

(71) Applicant: SHENZHEN MINDRAY BIO-MEDICAL ELECTRONICS CO., LTD., Shenzhen (CN)

(72) Inventors: Hui Yu, Shenzhen (CN); Shuiyang Pan, Shenzhen (CN); Wenyu Ye, Shenzhen (CN); Jian Cen, Shenzhen (CN); Fang Liu, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 1316 days.

(21) Appl. No.: 14/649,872

(22) PCT Filed: Sep. 9, 2013

(86) PCT No.: PCT/CN2013/083093
§ 371 (c)(1),
(2) Date: Sep. 28, 2015

(87) PCT Pub. No.: WO2014/086176
PCT Pub. Date: Jun. 12, 2014

(65) Prior Publication Data
US 2016/0015312 A1 Jan. 21, 2016

(30) Foreign Application Priority Data
Dec. 5, 2012 (CN) .......................... 2012 1 0516753

(51) Int. Cl.
*A61B 5/00* (2006.01)
*A61B 5/11* (2006.01)
*A61N 1/20* (2006.01)

(52) U.S. Cl.
CPC .......... *A61B 5/4519* (2013.01); *A61B 5/1121* (2013.01); *A61B 5/4836* (2013.01);
(Continued)

(58) Field of Classification Search
CPC combination set(s) only.
See application file for complete search history.

(56) References Cited

U.S. PATENT DOCUMENTS

| 6,315,736 B1 | 11/2001 | Tsutsumi et al. |
| 8,187,209 B1 | 5/2012 | Giuffrida |

(Continued)

FOREIGN PATENT DOCUMENTS

| CN | 201643223 U | 11/2010 |
| CN | 102525490 A | 7/2012 |
| WO | 2008031209 A1 | 3/2008 |

*Primary Examiner* — Sean P Dougherty
(74) *Attorney, Agent, or Firm* — Kory D. Christensen

(57) ABSTRACT

Disclosed are a method for measuring the level of muscle relaxation, a device thereof and an apparatus for measuring muscle relaxation, and the method respectively obtains the sampled values of the acceleration and angular velocity of the measurement site via an acceleration sensor and an angular velocity sensor or a speed sensor and an angular velocity sensor, in order to calculate the degree of muscle relaxation according to the sampled values of the acceleration and angular velocity. As the calculated results combine the sampled values of the acceleration and angular velocity of the measurement site, the accuracy of the calculated results is higher. Moreover, the measurement combines an acceleration sensor and an angular velocity sensor or a speed sensor and an angular velocity sensor, so that the apparatus for measuring muscle relaxation can be placed in any (Continued)

position of the measurement site without influencing the accuracy of the measured results.

10 Claims, 5 Drawing Sheets

(52) U.S. Cl.
CPC .............. *A61B 5/7278* (2013.01); *A61N 1/20* (2013.01); *A61B 5/4821* (2013.01); *A61B 2562/0219* (2013.01); *A61B 2562/222* (2013.01)

(56) References Cited

U.S. PATENT DOCUMENTS

| | | | | |
|---|---|---|---|---|
| 9,084,550 B1* | 7/2015 | Bartol | ................. | A61B 5/0488 |
| 10,022,545 B1* | 7/2018 | Giuffrida | ............. | A61B 5/0488 |
| 2007/0027631 A1 | 2/2007 | Cabrera et al. | | |
| 2009/0171381 A1* | 7/2009 | Schmitz | ................ | A61B 5/0488 |
| | | | | 606/167 |
| 2009/0221937 A1* | 9/2009 | Smith | .................... | A61B 5/1117 |
| | | | | 600/595 |
| 2010/0174342 A1* | 7/2010 | Boston | ................. | A61N 1/0452 |
| | | | | 607/48 |
| 2011/0224503 A1* | 9/2011 | Cusimano Reaston | ....................... | |
| | | | | A61B 5/0002 |
| | | | | 600/301 |
| 2011/0230782 A1* | 9/2011 | Bartol | ................. | A61B 5/0488 |
| | | | | 600/546 |
| 2013/0123568 A1* | 5/2013 | Hamilton | ........... | A61N 1/36003 |
| | | | | 600/13 |
| 2013/0123665 A1* | 5/2013 | Mariani | ................ | A61B 5/1038 |
| | | | | 600/592 |
| 2013/0331711 A1* | 12/2013 | Mathur | ................. | A61B 5/1106 |
| | | | | 600/483 |
| 2015/0032022 A1* | 1/2015 | Stone | ................. | A61B 5/04001 |
| | | | | 600/547 |

* cited by examiner

METHOD FOR MEASURING LEVEL OF MUSCLE RELAXATION, PROCESSING DEVICE THEREOF AND INSTRUMENT FOR MEASURING MUSCLE RELAXATION

TECHNICAL FIELD

The present application relates to medical devices, and particularly to a method for measuring the level of muscle relaxation, a processing device thereof and an apparatus for measuring muscle relaxation.

BACKGROUND

A patient may generate unexpected movement during surgical proceedings or may be required to relax his/her muscles to a certain degree. Therefore, a drug such as a muscle relaxant needs to be injected into the patient. After injection of the drug, monitoring muscle relaxation is usually performed on the patient to evaluate the degree of muscle relaxation. The degree of muscle relaxation can be detected by measuring the contraction strength of the adductor brevis of the patient's thumb. This is because the contraction strength reflects the degree of muscle relaxation. The strength is proportional to the acceleration according to Newton's law. Accordingly, the contraction strength of the adductor brevis of the thumb can be indirectly obtained by measuring the acceleration generated by movement of the thumb.

The level of muscle relaxation is usually measured by monitoring acceleration values generated by moving the thumb to output acceleration sampled values, and deriving angular velocity values by the acceleration values with some motion prediction. However, there exists bias between the motion prediction and actual movement of the thumb, resulting in inaccurate measurement of muscle relaxation. For example, suppose that the thumb moves in a circle around a fixed point (e.g., the base of the thumb), then a linear velocity can be acquired by the time integral of acceleration, and an angular velocity can be computed by dividing the linear velocity by an estimated length of the thumb. Thus all information required by measuring muscle relaxation can be obtained. Obviously, the actual movement of the thumb is not entirely a circular motion; therefore, such motion prediction may introduce an error in the measurement result.

SUMMARY

According to a first aspect of the present application, provided is a method for measuring the level of muscle relaxation, comprising: acquiring acceleration sampled values of a measurement site from an acceleration sensor or a speed sensor, acquiring angular velocity sampled values of the measurement site from an angular velocity sensor, and calculating the level of muscle relaxation according to the acceleration sampled values and the angular velocity sampled values.

According to a second aspect of the present application, provided is a processing device for measuring muscle relaxation, comprising: a receiving unit for acquiring acceleration sampled values of a measurement site from an acceleration sensor or a speed sensor, and for acquiring angular velocity sampled values of the measurement site from an angular velocity sensor; and a processing module for calculating the level of muscle relaxation according to the acceleration sampled values and the angular velocity sampled values.

According to a third aspect of the present application, provided is an apparatus for measuring muscle relaxation, comprising: a constant-current source for generating stimulative current and through a current output thereof, applying current stimulation on a subject to be detected; a response-signal extraction end comprising an acceleration sensor and an angular velocity sensor or comprising a speed sensor and an angular velocity sensor; and a processor connected with the constant-current source for controlling the constant-current source to generate stimulative current, the processor further communicatively connected with the response-signal extraction end for acquiring acceleration sampled values and angular velocity sampled values from motion information outputted by the response-signal extraction end, and calculating the level of muscle relaxation according to the acceleration sampled values and the angular velocity sampled values.

In the present application, with an angular velocity sensor, sampled values of acceleration and angular velocity of a measurement site can be obtained when detecting the level of muscle relaxation. According to the sampled values of the acceleration and angular velocity, the level of muscle relaxation can be computed. Since the computed result associates with the sampled values of the acceleration and angular velocity of the measurement site, the accuracy of the computed result is improved. Moreover, the measurement combines an acceleration sensor and an angular velocity sensor or a speed sensor and an angular velocity sensor to acquire the sampled values of acceleration and angular velocity of the measurement site, so that an apparatus for measuring muscle relaxation can be placed in any position of the measurement site without influencing the accuracy of the measured result.

BRIEF DESCRIPTION OF THE DRAWINGS

FIG. 3b is a reference coordinate system obtained by rotating a coordination system in which the acceleration sensor lies in FIG. 3a;

DETAILED DESCRIPTION

The present application will be further described by the following detailed description of specific embodiments with the accompanying drawings.

First Embodiment

Figure 1A:
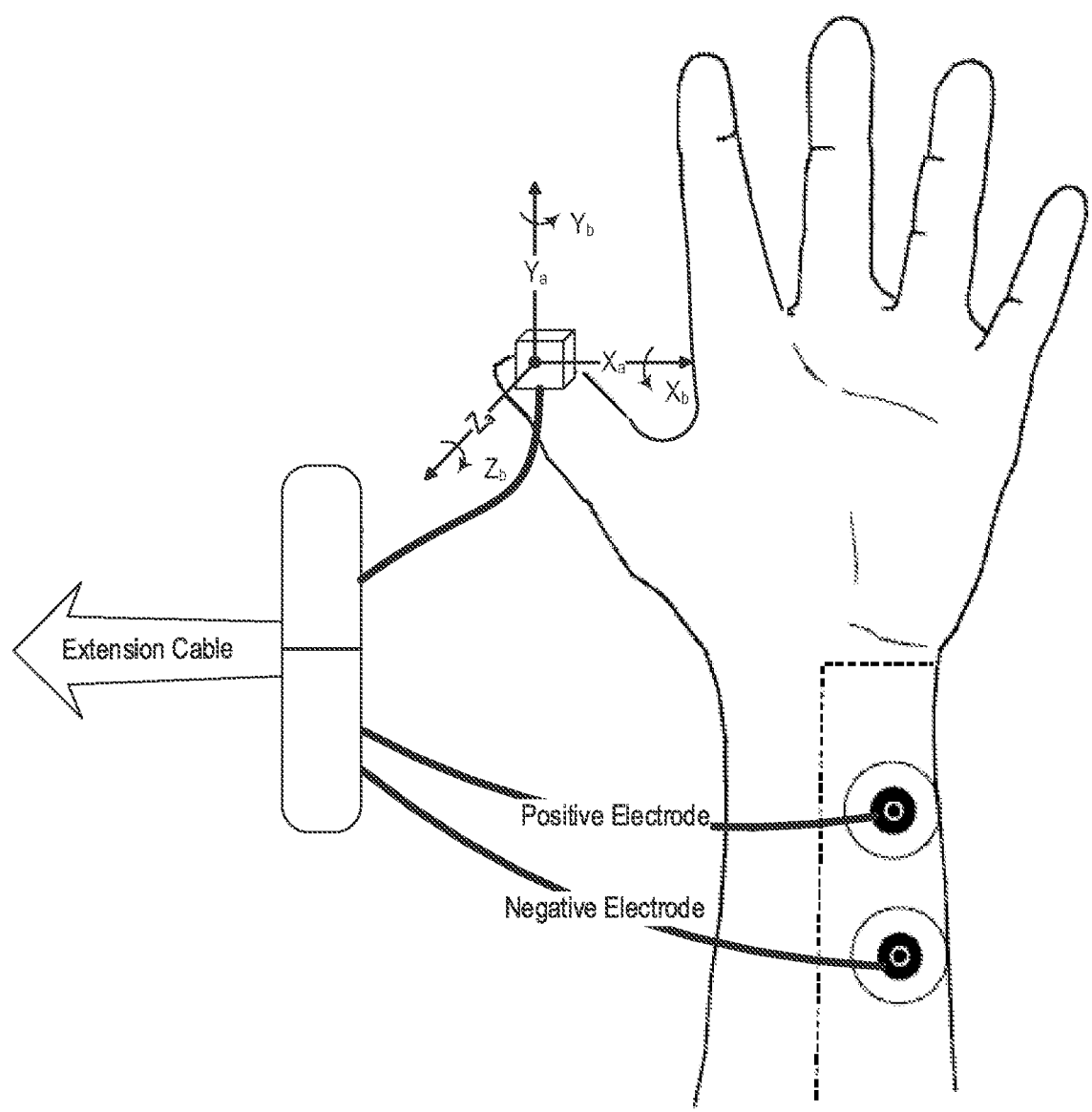
FIG. 1a is a schematic view showing measuring the level of muscle relaxation of a thumb with an apparatus for measuring muscle relaxation in an embodiment of the present application.
Figure 1B:
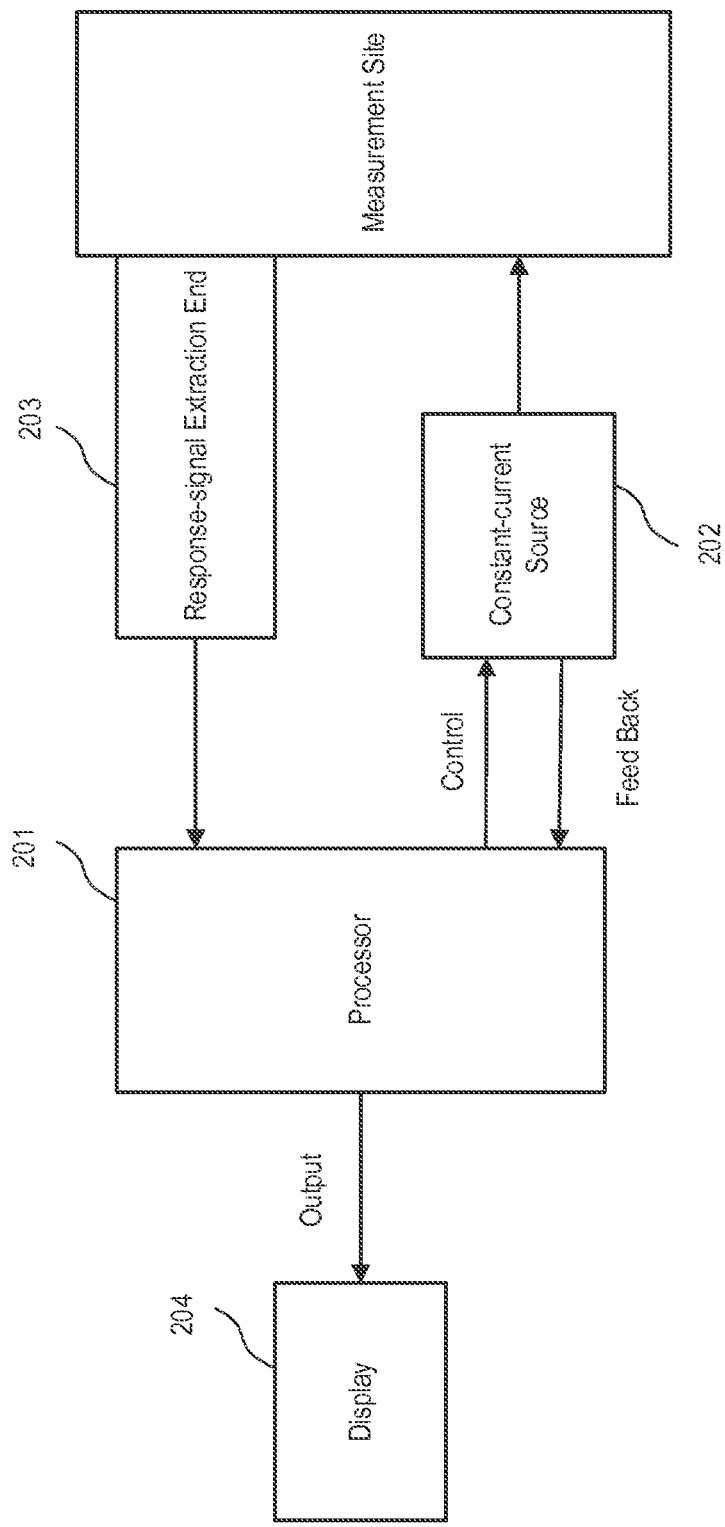
FIG. 1b is a schematically structural view of an apparatus for measuring muscle relaxation in an embodiment of the present application.

Please refer to FIG. 1a and FIG. 1b, which show an apparatus for measuring muscle relaxation in this embodiment that includes a processor 201, a constant-current source 202 and a response-signal extraction end 203.

The processor 201 is connected with the constant-current source 202 for controlling the constant-current source 202 to generate stimulative current. When measuring, a current output of the constant-current source 202 is connected to two electrodes via a pair of cables respectively. The two electrodes can be attached to a part of a person being measured. As shown in FIG. 1a, the two electrodes are attached to a wrist of the person being measured, and the response-signal extraction end 203 is attached to a thumb of the person being measured. When the constant-current source 202 outputs stimulative current, the person being measured may get an electric shock at the wrist, and the thumb may be moved due to the stimulation. The response-signal extraction end 203 may sense the movement of the thumb and output motion information.

The processor 201 is also communicatively connected with the response-signal extraction end 203; exchanges data with the response-signal extraction end 203, for example, receiving motion information outputted by the response-signal extraction end 203; and calculates the level of muscle relaxation based on the motion information. In another embodiment, the processor 201 may also send information about configuration, calibration and/or identity to the response-signal extraction end 203. The communication connection includes wired and wireless connection.

In an embodiment, the response-signal extraction end 203 includes an acceleration sensor and an angular velocity sensor. The acceleration sensor refers to a sensor which can sense an acceleration of a subject to be measured and convert the acceleration into electrical signals for outputting. The angular velocity sensor refers to a sensor which can sense an angular velocity of the subject to be measured and convert the angular velocity into electrical signals for outputting. In the first embodiment, the acceleration sensor can output real-time acceleration information, and the angular velocity sensor can output real-time angular velocity information. The response-signal extraction end 203 transmits the information about acceleration and angular velocity to the processor 201. The information about acceleration and angular velocity may be analog electrical signals, digital signals, continuous waveform data or discrete sampled values. The processor 201 may acquire sampled values of acceleration and angular velocity from the information about acceleration and angular velocity, and calculate the level of muscle relaxation based on the sampled values of acceleration and angular velocity.

In another embodiment, the response-signal extraction end 203 includes a speed sensor and an angular velocity sensor. The speed sensor refers to a sensor which can sense a kinematic velocity of the subject to be measured. The response-signal extraction end 203 can directly output information about velocity and time, or it may calculate acceleration based on the information about velocity and time, and convert the acceleration into electrical signals for outputting. Accordingly, besides the information about angular velocity, the information acquired by the processor 201 from the response-signal extraction end 203 may also include information about speed or acceleration. When acquiring speed information from the response-signal extraction end 203, the processor 201 can calculate acceleration based on the information about speed and time. Then the processor 201 can calculate the level of muscle relaxation based on the information about acceleration and angular velocity.

The processor 201 may, according to the sampled values of acceleration and angular velocity, calculate the level of muscle relaxation by adopting a following scheme:

The processor 201 may, according to initial components of gravity acceleration, compute rotation angles from an initial coordinate system to a reference coordinate system, calculate a transition matrix from the initial coordinate system to the reference coordinate system based on the rotation angles, and obtain a transition matrix from the reference coordinate system to the initial coordinate system based on the transition matrix from the initial coordinate system to the reference coordinate system. The reference coordinate system, which corresponds to a transition matrix, may be acquired by converting the coordinate system in which an initial acceleration lies (i.e., the initial coordinate system). Different transition matrixes may correspond to different reference systems, which can be determined according to the actual situation. In a simple case, the coordinate system in which the initial acceleration lies is converted so as to make the gravity acceleration appear only a component on a single dimension of the reference coordinate system and other components thereof on other dimensions are zero, which may simplify further processing.

The processor 201 may analyze the sampled values of the angular velocity to acquire rotation angles along the moving direction of an individual axis about the measurement site, and calculate motion vectors based on the rotation angles along the moving direction of an individual axis about the measurement site. In a specific example, the processor 201 may calculate the motion vectors with an inertial navigation algorithm which may refer to an algorithm like Picord algorithm or multi-sample rotation vector algorithm adopted to solve a pose of an object in motion based on data measured by an angular velocity sensor like a gyroscope to obtain the vectors of motion state of the measurement site. The vectors of motion state may represent motion information about the part to be measured when the part is moving after it is stimulated. According to the vectors of motion state, a transition matrix from the initial coordinate system to a kinetic coordinate system can be acquired. The motion information at least includes information of acceleration or speed and angular velocity about the measurement site when the part is moving.

The processor 201 may acquire the initial components of the gravity acceleration in the initial coordinate system at time $t_0$ with the acceleration sensor or the speed sensor, where the time $t_0$ may be any time before giving out an electrical stimulation and the measurement site staying still; then calculate the transition matrix from the reference coordinate system to the initial coordinate system at the time $t_0$ based on the initial components of the gravity acceleration; compute the transition matrix from the initial coordinate system to the kinetic coordinate system based on the sampled values of the angular velocity; and acquire the transition matrix from the reference coordinate system to the kinetic coordinate system according to the transition matrix from the reference coordinate system to the initial coordinate system and the transition matrix from the initial coordinate system to the kinetic coordinate system.

The processor 201 may calculate the transition matrix from the referent coordinate system to the kinetic coordinate system according to the acceleration sampled values outputted by the acceleration sensor or the speed sensor and the angular velocity sampled values outputted by the angular velocity sensor at time $t_k$, and acquire components of the gravity acceleration in the acceleration sensor coordinate system or the speed sensor coordinate system according to components of the gravity acceleration projected in the reference coordinate system and the transition matrix from the reference coordinate system to the kinetic coordinate system, where the time $t_k$ may be any time after giving out the electrical stimulation, the kinetic coordinate system may be the acceleration sensor coordinate system or the speed sensor coordinate system at the time $t_k$, the components of the gravity acceleration in the reference coordinate system are [0, 1, 0].

The processor 201 may calculate components of the gravity acceleration in the acceleration sensor or speed sensor coordinate system according to the sampled values of acceleration and angular velocity, subtract the components of the gravity acceleration from the acceleration sampled values to obtain real acceleration components in the acceleration sensor or speed sensor coordinate system, perform a composition operation on the real acceleration components to obtain acceleration values generated by actual movement of the measurement site, and calculate the level of muscle relaxation based on the acceleration values.

Since the apparatus for measuring muscle relaxation senses the movement of the measurement site with the acceleration sensor and the angular velocity sensor to output real-time sampled values of acceleration and angular velocity, and computes the level of muscle relaxation based on the sampled values of acceleration and angular velocity, the computed results associate with the sampled values of the acceleration and angular velocity of the measurement site and the influence of gravity is eliminated during the computation, which improves the accuracy of the computed results. Moreover, the device for measuring muscle relaxation of the apparatus can be placed in any position of the measurement site without influencing the accuracy of the measured result.

In a specific example, the angular velocity sensor can particularly be a gyro sensor.

In this embodiment, the apparatus for measuring muscle relaxation further includes a display 204 to which the processor 201 sends the computed results of the level of muscle relaxation for display.

The way the processor 201 measures muscle relaxation based on the sampled values of acceleration and angular velocity is by measuring the level of muscle relaxation of a thumb with the response-signal extraction end 203 in a three-dimensional coordinate system.

The measuring device of the apparatus for measuring muscle relaxation is mounted at any position on the thumb and has a same kinestate with the thumb, in this case, $X_a$, $Y_a$, $Z_a$ are the three axes of the acceleration sensor coordinate system respectively, and $X_b$, $Y_b$, $Z_b$ are the three axes of the angular velocity sensor coordinate system respectively. The subject to be measured is stimulated with electrical current by the apparatus through the two electrodes connected on the wrist, and the thumb moves when it is stimulated. The acceleration sensor and the angular velocity sensor output triaxial acceleration sampled values and triaxial angular velocity sampled values respectively when the thumb is moved. The processor 201 may calculate the components of the gravity acceleration at the three axes of the acceleration sensor coordinate system according to the triaxial acceleration sampled values and triaxial angular velocity sampled values, subtract the components of the gravity acceleration at the three axes of the acceleration sensor coordinate system from the triaxial acceleration sampled values to obtain real acceleration components of the measurement site, perform a composition operation on the real acceleration component to obtain acceleration values generated by actual movement of the measurement site, and calculate the level of muscle relaxation based on the acceleration values.

When the measurement site is still, the initial coordinate system of the acceleration sensor is $A_{r0}$ and the reference coordinate system R is obtained by rotating the initial coordinate system $A_{r0}$. In the specific example, one axis of the reference coordinate system R coincides with the direction of the gravity acceleration, for example, as to a three-dimensional coordinate system, the components of the gravity acceleration in the reference coordinate system can be [0, 1, 0]. The reference coordinate system R can be obtained by rotating the initial coordinate system. For example, the reference coordinate system R can be obtained by rotating the initial coordinate system $A_{r0}$ by an angle $\varphi$ along z axis then rotating by an angle $\theta$ along x axis, where the rotation angles are $\varphi=\cos^{-1}(y_{A_{r0}}/\sqrt{x_{A_{r0}}^2+y_{A_{r0}}^2})$ and $\theta=\sin^{-1}(z_{A_{r0}}/\sqrt{x_{A_{r0}}^2+y_{A_{r0}}^2+z_{A_{r0}}^2})$, $A_{A_{r0}}$, $y_{A_{r0}}$, $z_{A_{r0}}$ are acceleration components sensed by the acceleration sensor along x, y, z axes respectively in the initial coordinate system $A_{r0}$.

The processor 201 may acquire a transition matrix of the initial coordinate system $A_{r0}$ around the z axis based on the rotation angle $\varphi$:

$$C_Z = \begin{bmatrix} \cos\varphi & \sin\varphi & 0 \\ -\sin\varphi & \cos\varphi & 0 \\ 0 & 0 & 1 \end{bmatrix},$$

The processor 201 may acquire a transition matrix of the initial coordinate system $A_{r0}$ around the x axis based on the rotation angle $\theta$:

$$C_X \begin{bmatrix} 1 & 0 & 0 \\ 0 & \cos\theta & \sin\theta \\ 0 & -\sin\theta & \cos\theta \end{bmatrix},$$

The processor 201 may acquire a transition matrix from the reference coordinate system R to the initial coordinate system $A_{r0}$ based on the transition matrixes $C_Z$ and $C_X$:

$$C_R^{A_{r0}} = C_Z \cdot C_X)^T;$$

Of course, it can be understood by those skilled in the art that the reference coordinate system R can also be obtained by rotating the initial coordinate system $A_{r0}$ in other rotation manners; in this case, the transition matrixes acquired by rotating the initial coordinate system $A_{r0}$ around the z, x axes by the processor 201 may be different from those mentioned above.

When the measurement site is moved by current stimulation, the processor 201 performs an integral operation respectively on the triaxial angular velocity sampled values outputted by the angular velocity sensor to acquire the rotation angles $\Delta\theta_x$, $\Delta\theta_y$, $\Delta\theta_z$ of the measurement site along triaxial directions, and according to the rotation angles $\Delta\theta_x$, $\Delta\theta_y$, $\Delta\theta_z$ of the measurement site along triaxial directions, acquire a quaternion $q_0(t_k)$, $q_1(t_k)$, $q_2(t_k)$, $q_3(t_k)$ which can represent motion information about the measurement site when it moves after it is stimulated. The motion information may at least include information about acceleration and angular velocity of the measurement site when it moves. In the embodiment, the processor 201 may calculate the quaternion of the measurement site in motion with the Picord algorithm.

$$\begin{bmatrix} q_0(t_k) \\ q_1(t_k) \\ q_2(t_k) \\ q_3(t_k) \end{bmatrix} =$$

$$\begin{bmatrix} \cos\frac{\Delta\theta}{2} & -\frac{\Delta\theta_x}{\Delta\theta}\sin\frac{\Delta\theta}{2} & -\frac{\Delta\theta_y}{\Delta\theta}\sin\frac{\Delta\theta}{2} & -\frac{\Delta\theta_z}{\Delta\theta}\sin\frac{\Delta\theta}{2} \\ \frac{\Delta\theta_x}{\Delta\theta}\sin\frac{\Delta\theta}{2} & \cos\frac{\Delta\theta}{2} & \frac{\Delta\theta_z}{\Delta\theta}\sin\frac{\Delta\theta}{2} & -\frac{\Delta\theta_y}{\Delta\theta}\sin\frac{\Delta\theta}{2} \\ \frac{\Delta\theta_y}{\Delta\theta}\sin\frac{\Delta\theta}{2} & -\frac{\Delta\theta_z}{\Delta\theta}\sin\frac{\Delta\theta}{2} & \cos\frac{\Delta\theta}{2} & \frac{\Delta\theta_x}{\Delta\theta}\sin\frac{\Delta\theta}{2} \\ \frac{\Delta\theta_z}{\Delta\theta}\sin\frac{\Delta\theta}{2} & \frac{\Delta\theta_y}{\Delta\theta}\sin\frac{\Delta\theta}{2} & -\frac{\Delta\theta_x}{\Delta\theta}\sin\frac{\Delta\theta}{2} & \cos\frac{\Delta\theta}{2} \end{bmatrix} \begin{bmatrix} q_0(t_{k-1}) \\ q_1(t_{k-1}) \\ q_2(t_{k-1}) \\ q_3(t_{k-1}) \end{bmatrix}$$

where, $$\Delta\theta = \sqrt{\Delta\theta_x^2 + \Delta\theta_y^2 + \Delta\theta_z^2},$$

$$\begin{bmatrix} q_0(t_0) \\ q_1(t_0) \\ q_2(t_0) \\ q_3(t_0) \end{bmatrix} = \begin{bmatrix} 1 \\ 0 \\ 0 \\ 0 \end{bmatrix}.$$

Of course, the quaternion of the measurement site in motion can also be calculated with the multi-sample rotation vector algorithm. The Picord algorithm used to calculate the quaternion by the processor 201 in the embodiment should not be considered to limit the present application.

Then the processor 201 may, according to the acquired quaternion, acquire a transition matrix from the initial coordinate system $A_{t0}$ to the kinetic coordinate system $A_{tk}$ in which the acceleration sensor lies at any time when the measurement site moves after it is stimulated:

$$C_{A_{t0}}^{A_{tk}} = \begin{bmatrix} q_0(t_k)^2 + q_1(t_k)^2 - q_2(t_k)^2 - q_3(t_k)^2 & 2[q_1(t_k)q_2(t_k) - q_0(t_k)q_3(t_k)] & 2[q_1(t_k)q_3(t_k) + q_0(t_k)q_2(t_k)] \\ 2[q_1(t_k)q_2(t_k) + q_0(t_k)q_3(t_k)] & q_0(t_k)^2 - q_1(t_k)^2 + q_2(t_k)^2 - q_3(t_k)^2 & 2[q_2(t_k)q_3(t_k) - q_0(t_k)q_1(t_k)] \\ 2[q_1(t_k)q_3(t_k) - q_0(t_k)q_2(t_k)] & 2[q_2(t_k)q_3(t_k) + q_0(t_k)q_1(t_k)] & q_0(t_k)^2 - q_1(t_k)^2 - q_2(t_k)^2 + q_3(t_k)^2 \end{bmatrix}$$

The processor 201 may calculate a transition matrix from the reference coordinate system R to the kinetic coordinate system $A_{tk}$ with an equation $C_R^{A_{tk}} = C_{A_{t0}}^{A_{tk}} C_R^{A_{t0}}$.

In this case, the processor 201 may multiply the components of the gravity acceleration projected in the reference coordinate system by the transition matrix from the reference coordinate system to the kinetic coordinate system to acquire triaxial components of the gravity acceleration in the acceleration sensor coordination system, i.e., $[G_x, G_y, G_z]^T = C_R^{A_{tk}} [0, 1, 0]^T$, where the components of the gravity acceleration projected in the reference coordinate system are $[0, 1, 0]^T$.

Suppose that the response-signal extraction end 203 lies in a one-dimensional or two-dimensional coordinate system, with the above idea, similarly, the influence of gravity acceleration can also be eliminated by coordinate transformation based on sampled values of acceleration and angular velocity.

In the apparatus for measuring muscle relaxation provided in the embodiment, by means of subtracting the components of the gravity acceleration in the acceleration sensor coordination system from the acceleration sampled values to obtain real acceleration components of the measurement site, the influence of the gravity acceleration to the measured results can be eliminated, which improves the accuracy of the measurement.

The processor 201 can be one or more integrated chips with recorded programs which can be performed to achieve the above functions.

Second Embodiment

Figure 2:
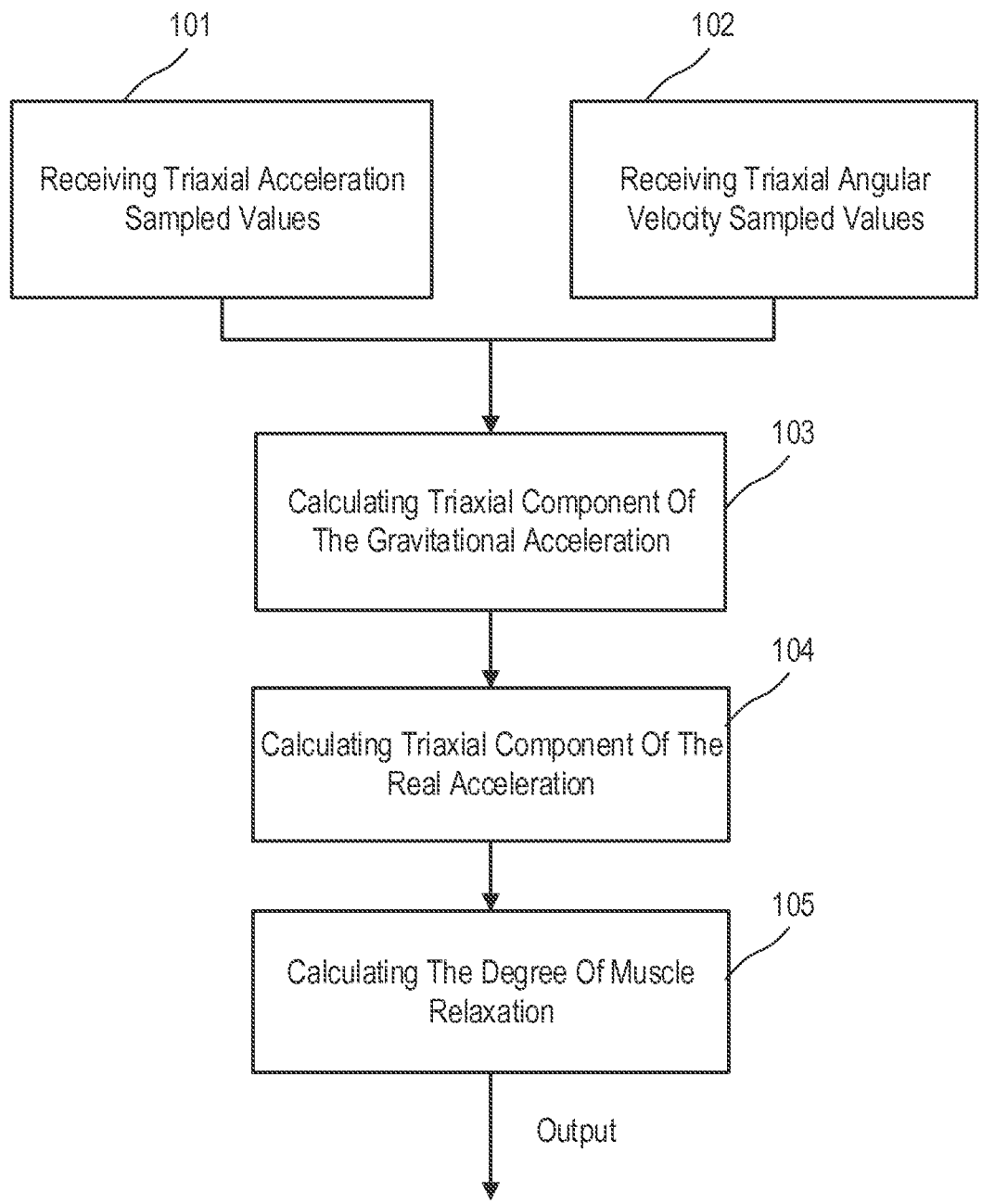
FIG. 2 is a flowchart of a method for measuring the level of muscle relaxation in an embodiment of the present application.

Please refer to FIG. 2. By taking an example of a three-dimensional coordinate system, the method for measuring the level of muscle relaxation provided in this embodiment may include the following steps:

Step 101, when the subject to be measured moves after it is current stimulated, outputting triaxial acceleration sampled values about the part being measured by the acceleration sensor.

Step 102, outputting triaxial angular velocity sampled values about the part being measured by the angular velocity sensor.

Step 103, acquiring triaxial components of the gravity acceleration in the acceleration sensor coordinate system according to axial acceleration sampled values and axial angular velocity sampled values by the apparatus.

Step 104, subtracting the triaxial components of the gravity acceleration in the acceleration sensor coordinate system obtained in step 103 from the triaxial acceleration sampled values to obtain real acceleration components of the part being measured by the apparatus.

Step 105, performing a composition operation on the real acceleration components of the part being measured obtained in step 104 to obtain an acceleration value $\sqrt{a_x^2 + a_y^2 + a_z^2}$ generated by actual movement of the part being measured, then extracting effective peak information of the composite acceleration which is regarded as real acceleration generated by the movement of the part being measured, taking the real acceleration to calculate the level of muscle relaxation, and outputting the calculated results.

Figure 3A:
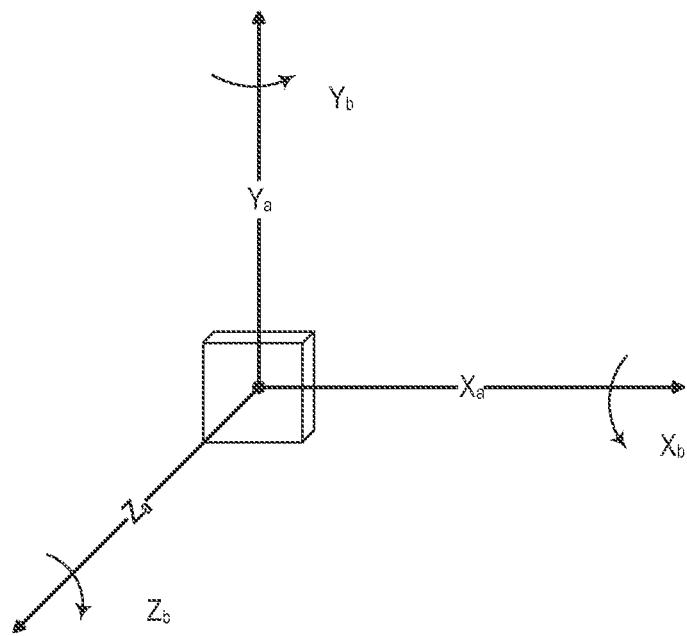
FIG. 3a is a coordination system in which an acceleration sensor and an angular velocity sensor lie in an embodiment of the present application.
Figure 3B:
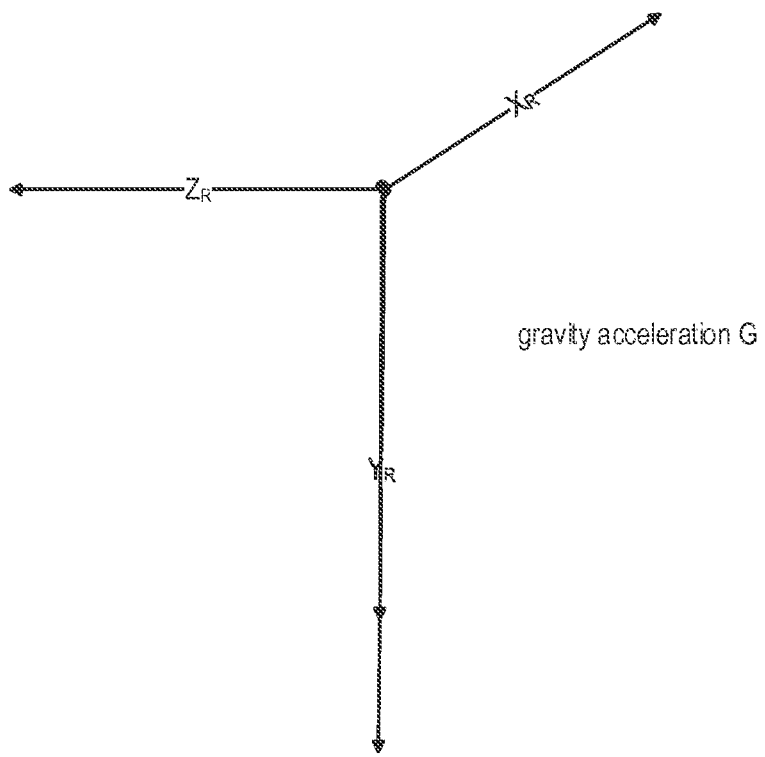

In the embodiment, the step 103 where the apparatus acquires triaxial components of the gravity acceleration in the acceleration sensor coordinate system according to axial sampled values of acceleration and angular velocity may comprise:

Please refer to FIG. 3a, which shows a coordinate system in which the acceleration sensor and the angular velocity sensor lie, where $X_a$, $Y_a$, $Z_a$ represent three axes of the acceleration sensor coordinate system, and $X_b$, $Y_b$, $Z_b$ represent three axes of the angular velocity sensor coordinate system. Please refer to FIG. 3b, which shows a reference coordinate system obtained by rotating the acceleration sensor coordinate system of FIG. 3a, where $X_R$, $Y_R$, $Z_R$ represent three axes of the reference coordinate system R; in the reference coordinate system R, the components of the gravity acceleration at the three axes are [0, 1, 0].

When the part being measured is still, the initial coordinate system of the acceleration sensor is $A_{t0}$, the reference coordinate system R is obtained by rotating the initial coordinate system $A_{t0}$, and the components of the gravity acceleration in the reference coordinate system can be [0, 1, 0]. Preferably, in the embodiment, the reference coordinate system R can be obtained by rotating the initial coordinate system $A_{t0}$ by an angle $\varphi$ along the z axis then rotating by an angle $\theta$ along the x axis, where the rotation angles are $\varphi=\cos^{-1}(y_{A_{t0}}/\sqrt{x_{A_{t0}}^2+y_{A_{t0}}^2})$ and $\theta=\sin^{-1}(z_{A_{t0}}/\sqrt{x_{A_{t0}}^2+y_{A_{t0}}^2+z_{A_{t0}}^2})$, and $x_{A_{t0}}$, $y_{A_{t0}}$, $z_{A_{t0}}$, are acceleration components sensed by the acceleration sensor along the x, y, z axes respectively in the initial coordinate system $A_{t0}$.

A transition matrix of the initial coordinate system $A_{t0}$ around the z axis can be acquired based on the rotation angle $\varphi$:

$$C_Z = \begin{bmatrix} \cos\varphi & \sin\varphi & 0 \\ -\sin\varphi & \cos\varphi & 0 \\ 0 & 0 & 1 \end{bmatrix},$$

A transition matrix of the initial coordinate system $A_{t0}$ around the x axis can be acquired based on the rotation angle $\theta$:

$$C_X \begin{bmatrix} 1 & 0 & 0 \\ 0 & \cos\theta & \sin\theta \\ 0 & -\sin\theta & \cos\theta \end{bmatrix}.$$

A transition matrix from the reference coordinate system R to the initial coordinate system $A_{t0}$ can be acquired based on the transition matrixes $C_Z$ and $C_X$:

$$C_R^{A_{t0}}=(C_Z \cdot C_X)^T.$$

Of course, it can be understood by those skilled in the art that the reference coordinate system R can also be obtained by rotating the initial coordinate system $A_{t0}$ in other rotation manners; in this case, the transition matrixes acquired by rotating the initial coordinate system $A_{t0}$ around the z, x axes may be different from those mentioned above.

When the measurement site is moved by current stimulation, the triaxial angular velocity sampled values outputted by the angular velocity sensor are analyzed respectively to acquire the rotation angles $\Delta\theta_x$, $\Delta\theta_y$, $\Delta\theta_z$ of the measurement site along triaxial directions, in the embodiment, the rotation angles of the measurement site along triaxial directions can be acquired by performing an integral operation, after which, according to the rotation angles $\Delta\theta_x$, $\Delta\theta_y$, $\Delta\theta_z$ of the measurement site along triaxial directions, the vectors of motion state which can represent motion information about the measurement site when it moves after it is stimulated can be acquired. The motion information may at least include information about acceleration and angular velocity of the measurement site in motion. In a specific example, the motion vectors can be a quaternion $q_0(t_k)$, $q_1(t_k)$, $q_2(t_k)$, $q_3(t_k)$. In the embodiment, the quaternion of the measurement site in motion can be calculated by the Picord algorithm:

$$\begin{bmatrix} q_0(t_k) \\ q_1(t_k) \\ q_2(t_k) \\ q_3(t_k) \end{bmatrix} =$$

$$\begin{bmatrix} \cos\frac{\Delta\theta}{2} & -\frac{\Delta\theta_x}{\Delta\theta}\sin\frac{\Delta\theta}{2} & -\frac{\Delta\theta_y}{\Delta\theta}\sin\frac{\Delta\theta}{2} & -\frac{\Delta\theta_z}{\Delta\theta}\sin\frac{\Delta\theta}{2} \\ \frac{\Delta\theta_x}{\Delta\theta}\sin\frac{\Delta\theta}{2} & \cos\frac{\Delta\theta}{2} & \frac{\Delta\theta_z}{\Delta\theta}\sin\frac{\Delta\theta}{2} & -\frac{\Delta\theta_y}{\Delta\theta}\sin\frac{\Delta\theta}{2} \\ \frac{\Delta\theta_y}{\Delta\theta}\sin\frac{\Delta\theta}{2} & -\frac{\Delta\theta_z}{\Delta\theta}\sin\frac{\Delta\theta}{2} & \cos\frac{\Delta\theta}{2} & \frac{\Delta\theta_x}{\Delta\theta}\sin\frac{\Delta\theta}{2} \\ \frac{\Delta\theta_z}{\Delta\theta}\sin\frac{\Delta\theta}{2} & \frac{\Delta\theta_y}{\Delta\theta}\sin\frac{\Delta\theta}{2} & -\frac{\Delta\theta_x}{\Delta\theta}\sin\frac{\Delta\theta}{2} & \cos\frac{\Delta\theta}{2} \end{bmatrix} \begin{bmatrix} q_0(t_{k-1}) \\ q_1(t_{k-1}) \\ q_2(t_{k-1}) \\ q_3(t_{k-1}) \end{bmatrix}$$

where, $$\Delta\theta = \sqrt{\Delta\theta_x^2 + \Delta\theta_y^2 + \Delta\theta_z^2},$$

$$\begin{bmatrix} q_0(t_0) \\ q_1(t_0) \\ q_2(t_0) \\ q_3(t_0) \end{bmatrix} = \begin{bmatrix} 1 \\ 0 \\ 0 \\ 0 \end{bmatrix}.$$

Of course, the quaternion of the measurement site in motion can also be calculated with the multi-sample rotation vector algorithm. The Picord algorithm used to calculate the quaternion in the embodiment should not be considered to limit the present application.

Then, according to the acquired quaternion, a transition matrix from the initial coordinate system $A_{t0}$ to the kinetic coordinate system $A_{tk}$ in which the acceleration sensor lies at any time when the measurement site moves after it is stimulated can be acquired:

$$C_{A_{t0}}^{A_{t_k}} = \begin{bmatrix} q_0(t_k)^2 + q_1(t_k)^2 - q_2(t_k)^2 - q_3(t_k)^2 & 2[q_1(t_k)q_2(t_k) - q_0(t_k)q_3(t_k)] & 2[q_1(t_k)q_3(t_k) + q_0(t_k)q_2(t_k)] \\ 2[q_1(t_k)q_2(t_k) + q_0(t_k)q_3(t_k)] & q_0(t_k)^2 + q_1(t_k)^2 + q_2(t_k)^2 - q_3(t_k)^2 & 2[q_2(t_k)q_3(t_k) - q_0(t_k)q_1(t_k)] \\ 2[q_1(t_k)q_3(t_k) - q_0(t_k)q_2(t_k)] & 2[q_2(t_k)q_3(t_k) + q_0(t_k)q_1(t_k)] & q_0(t_k)^2 - q_1(t_k)^2 - q_2(t_k)^2 + q_3(t_k)^2 \end{bmatrix}$$

Then, the transition matrix from the reference coordinate system R to the kinetic coordinate system $A_{tk}$ can be $C_R^{A_{tk}}=C_{A_{t0}}^{A_{tk}} C_R^{A_{t0}}$.

In this case, triaxial components of the gravity acceleration in the acceleration sensor coordination system can be obtained by multiplying the components of the gravity acceleration projected in the reference coordinate system by the transition matrix from the reference coordinate system to the kinetic coordinate system, i.e., $[G_x, G_y, G_z]^T = C_R^{A_k}[0, 1, 0]^T$, where the components of the gravity acceleration projected in the reference coordinate system are $[0, 1, 0]^T$.

In the method for measuring the level of muscle relaxation provided in the embodiment, the level of muscle relaxation can be calculated by sampled values of acceleration and angular velocity obtained by the acceleration sensor and the angular velocity sensor, and the influence of the gravity acceleration to the measured result can be eliminated during calculation, which can improve the accuracy of the measurement, so that a corresponding measuring device can be placed at any position of the measurement site without influencing the accuracy of the measured result.

Third Embodiment

Figure 4:
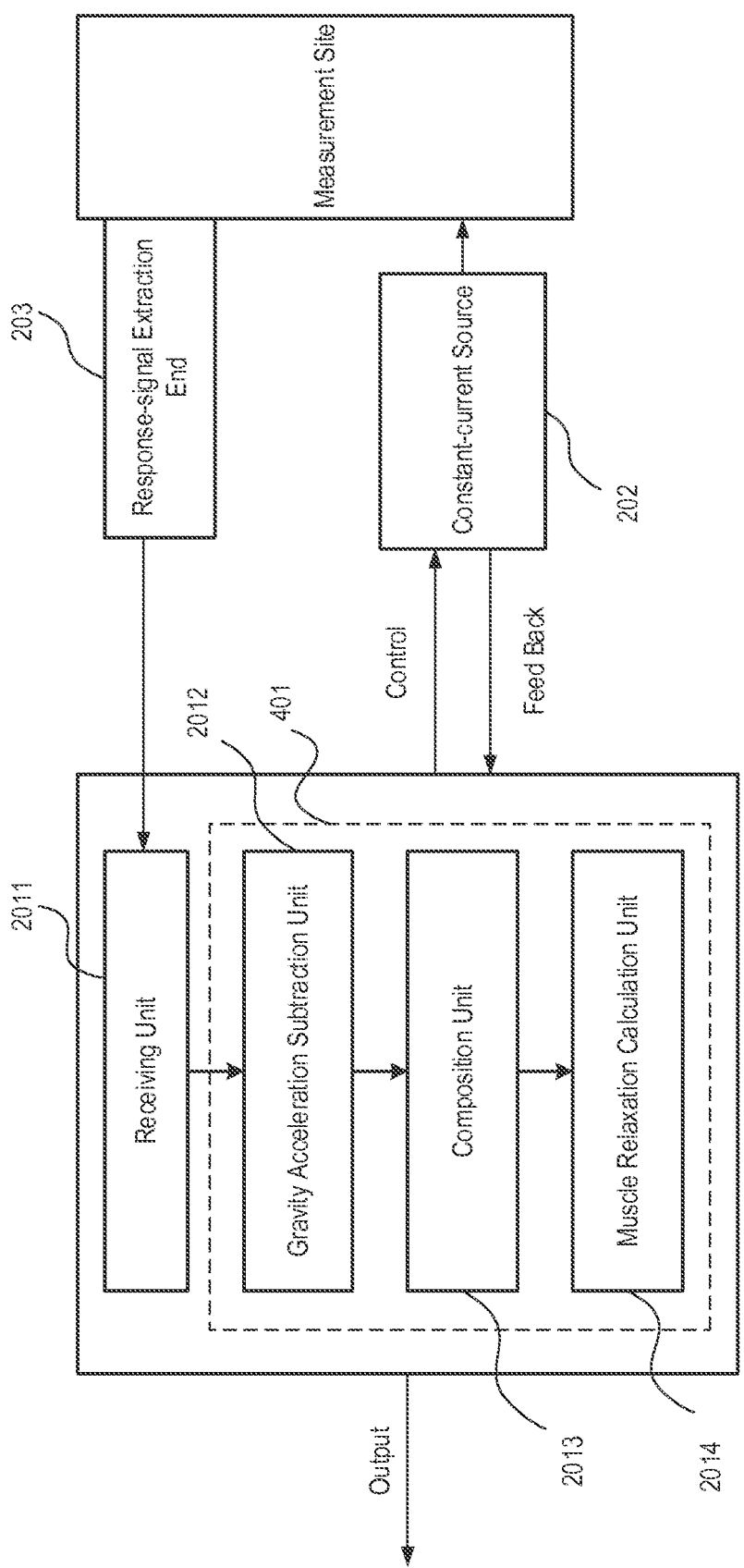
FIG. 4 is a schematic view showing modules of a processing device for measuring the level of muscle relaxation in an embodiment of the present application.

Please refer to FIG. 4, in which provided in the embodiment is a processing device for measuring the level of muscle relaxation which includes a processing module 401 and a receiving unit 2011.

When measuring, the processing module 401 is connected with the constant-current source 202 for controlling the constant-current source 202 to generate stimulative current so as to perform electrical stimulation on a subject to be detected through an electrical output of the constant-current source 202. The response-signal extraction end 203 is placed on the measurement site and has a same kinestate with the measurement site. When the measurement site moves after it is stimulated, the response-signal extraction end 203 senses and outputs motion information about the measurement site. The response-signal extraction output end 203 may include an acceleration sensor and an angular velocity sensor, or the response-signal extraction output end 203 may include a speed sensor and an angular velocity sensor. In the embodiment, the current output of the constant-current source 202 may also be connected with the processing module 401 for feeding back the outputted current to the processing module 401 for monitoring so as to ensure parameters like the outputted current remain within a range which the measurement site can tolerate.

The processor 401 may include a gravity acceleration subtraction unit 2012, a composition unit 2013 and a muscle relaxation calculation unit 2014. The receiving unit 2011 is used for acquiring acceleration sampled values of the part being measured from the acceleration sensor and angular velocity sampled values of the part being measured from the angular velocity sensor. The gravity acceleration subtraction unit 2012 may include a first subunit and a second subunit, wherein the first subunit is configured for calculating components of the gravity acceleration in the acceleration sensor coordinate system based on the sampled values of acceleration and angular velocity, and the second subunit is configured for subtracting the components of the gravity acceleration in the acceleration sensor coordinate system to obtain real acceleration components of the part being measured. The composition unit 2013 is configured for performing a composition operation on the real acceleration components to obtain an acceleration value $\sqrt{a_x^2+a_y^2+a_z^2}$ generated by actual movement of the measurement site. The muscle relaxation calculation unit 2014 is configured for taking the real acceleration to calculate the level of muscle relaxation and outputting the calculated results.

In the embodiment, the first subunit of the gravity acceleration subtraction unit 2012 may calculate a transition matrix from the reference coordinate system to the kinetic coordinate system according to the sampled values of acceleration and angular velocity of the part being measured obtained from an acceleration sensor and an angular velocity sensor at time $t_k$, and multiply the components of the gravity acceleration projected in the reference coordinate system by the transition matrix from the reference coordinate system to the kinetic coordinate system to acquire the components of the gravity acceleration in the kinetic coordinate system, where the time $t_k$ may be any time after giving out the electrical stimulation, the kinetic coordinate system may be the coordinate system in which the acceleration sensor lies at the time $t_k$, the reference coordinate system is obtained by rotating the initial coordinate system, the projecting components of the gravity acceleration may appear in the reference coordinate system, the initial coordinate system is a coordinate system in which the acceleration sensor or the speed sensor lies at any time before giving out an electrical stimulation and the measurement site staying still, for example, the components of gravity acceleration in the reference coordinate system are [0, 1, 0], and the components of the gravity acceleration projected in the reference coordinate system are $[0, 1, 0]^T$.

The first subunit may acquire initial gravity components of the gravity acceleration at time $t_0$ in the initial coordinate system when calculating the transition matrix from the reference coordinate system to the kinetic coordinate system, where the time $t_0$ is any time before giving out the electrical stimulation and the measurement site staying still; then calculate the transition matrix from the reference coordinate system to the initial coordinate system at time $t_0$ based on the initial gravity components; calculate the transition matrix from the initial coordinate system to the kinetic coordinate system based on angular velocity sampled values; and multiply the transition matrix from the reference coordinate system to the initial coordinate system by the transition matrix from the initial coordinate system to the kinetic coordinate system to calculate the transition matrix from the reference coordinate system to the kinetic coordinate system.

When calculating the transition matrix from the reference coordinate system to the initial coordinate system based on the initial gravity components, the first subunit may calculate the rotation angles from the initial coordinate system to the reference coordinate system based on the initial gravity components, calculate the transition matrix from the initial coordinate system to the reference coordinate system based on the rotation angles from the initial coordinate system to the reference coordinate system, and obtain the transition matrix from the reference coordinate system to the initial coordinate system based on the transition matrix from the initial coordinate system to the reference coordinate system. When calculating the transition matrix from the initial coordinate system to the kinetic coordinate system based on angular velocity sampled value, the first subunit may analyze the angular velocity sampled value to obtain rotation angles along the moving direction of an individual axis about the measurement site. In a specific example, the rotation angles of the measurement site along the moving direction of an individual axis about the measurement site can be acquired by performing an integral operation, then calculating the vectors of motion state representing motion information about the measurement site when it moves after it is stimulated according to the rotation angles of a measurement site along the moving direction of an individual axis about the measurement site, and acquiring the transition matrix from the initial coordinate system to the kinetic coordinate system based on the vectors of motion state. In a specific example, the vectors of motion state can be a quaternion, and the transition matrix from the initial coordinate system to the kinetic coordinate system can be acquired based on the quaternion.

In the processing device for measuring the level of muscle relaxation provided in the embodiment, the level of muscle relaxation can be calculated by sampled values of acceleration and angular velocity obtained by the acceleration sensor and the angular velocity sensor, and the influence of the gravity acceleration to the measured result can be eliminated during calculation, which can improve the accuracy of the measurement, so that the corresponding measuring device can be placed at any position of the measurement site without influencing the accuracy of the measured result.

The processor 201 can be one or more integrated chips recorded programs which can be performed to achieve the above functions.

Though the present application has been described in detailed by way of specified examples, the examples are used for helping to appreciate the present application, not to limit the present application. Those skilled in the art can change the above specified embodiments based on the spirit of the present application.

What is claimed is:

1. A method for measuring level of muscle relaxation, comprising:
   acquiring acceleration sampled values of a measurement site from an acceleration sensor or a speed sensor;
   acquiring angular velocity sampled values of the measurement site from an angular velocity sensor;
   calculating components of gravity acceleration in an acceleration sensor coordinate system or a speed sensor coordinate system according to the acceleration sampled values and the angular velocity sampled values;
   subtracting the components of gravity acceleration from the acceleration sampled values to obtain actual acceleration components in the acceleration sensor coordinate system or the speed sensor coordinate system;
   performing a composition operation on the actual acceleration components to obtain acceleration values generated by actual movement of the measurement site; and
   calculating a level of muscle relaxation according to the acceleration sampled values and the angular velocity sampled values using the acceleration values identified by subtracting the components of gravity acceleration from the acceleration sampled values;
   the step of calculating components of gravity acceleration in an acceleration sensor coordinate system or a speed sensor coordinate system according to the acceleration sampled values and the angular velocity sampled values comprises:
   calculating a transition matrix from a reference coordinate system to a kinetic coordinate system according to the acceleration sampled values from the acceleration sensor or the speed sensor and the angular velocity sampled values from the angular velocity sensor at time tk; where the time tk is any time after an electrical stimulation, the kinetic coordinate system is the acceleration sensor coordinate system or the speed sensor coordinate system at the time tk, the reference coordinate system is obtained by rotating an initial coordinate system, the initial coordinate system is the acceleration sensor coordinate system or the speed sensor coordinate system at any time before the electrical stimulation and the measurement site staying still.

2. The method for measuring level of muscle relaxation according to claim 1, wherein
   obtaining components of the gravity acceleration in the acceleration sensor coordinate system or the speed sensor coordinate system according to components of the gravity acceleration projected in the reference coordinate system and the transition matrix from the reference coordinate system to the kinetic coordinate system.

3. The method for measuring level of muscle relaxation according to claim 2, wherein the step of calculating a transition matrix from a reference coordinate system to a kinetic coordinate system comprises:
   acquiring initial components of gravity acceleration in the initial coordinate system at time t0 from the acceleration sensor or the speed sensor, the time t0 is any time before the electrical stimulation and the measurement site staying still;
   calculating a transition matrix from the reference coordinate system to the initial coordinate system at the time t0 based on the initial components of gravity acceleration;
   calculating a transition matrix from the initial coordinate system to the kinetic coordinate system based on the angular velocity sampled values; and
   according to the transition matrix from the reference coordinate system to the initial coordinate system and the transition matrix from the initial coordinate system to the kinetic coordinate system, obtaining the transition matrix from the reference coordinate system to the kinetic coordinate system.

4. The method for measuring level of muscle relaxation according to claim 3, wherein
   the step of calculating a transition matrix from the reference coordinate system to the initial coordinate system at the time t0 based on the initial components of gravity acceleration comprises:
   calculating rotation angles from the initial coordinate system to the reference coordinate system according to the initial components of gravity acceleration;
   calculating a transition matrix from the initial coordinate system to the reference coordinate system according to the rotation angles; and
   obtaining the transition matrix from the reference coordinate system to the initial coordinate system according to the transition matrix from the initial coordinate system to the reference coordinate system.

5. The method for measuring level of muscle relaxation according to claim 3, wherein the step of calculating a transition matrix from the initial coordinate system to the kinetic coordinate system based on the angular velocity sampled values comprises:
   analyzing the angular velocity sampled values to obtain rotation angles along moving direction of individual axis about the measurement site;
   obtaining vectors of motion state according to the rotation angles along moving direction of individual axis about the measurement site, the vectors of motion state representing motion information about the measurement site when the part is moving after got stimulated; and
   obtaining a transition matrix from the initial coordinate system to the kinetic coordinate system according to the vectors of motion state.

6. The method for measuring level of muscle relaxation according to claim 5, wherein the step of obtaining vectors of motion state according to the rotation angles along moving direction of individual axis about the measurement site comprises:
   according to the rotation angles along moving direction of individual axis about the measurement site, obtaining the vectors of motion state with an inertial navigation algorithm.

7. A processing device for measuring muscle relaxation, comprising:
   a receiving unit for acquiring acceleration sampled values of a measurement site from an acceleration sensor or a speed sensor, and for acquiring angular velocity sampled values of the measurement site from an angular velocity sensor; and a processing module for calculating a level of muscle relaxation according to the acceleration sampled values and the angular velocity sampled values, the processing module further comprising:
  a gravity acceleration subtraction unit comprising a first subunit for calculating components of gravity acceleration in an acceleration sensor coordinate system or a speed sensor coordinate system according to the acceleration sampled values and the angular velocity sampled values, and a second subunit for subtracting the components of gravity acceleration from the acceleration sampled values to obtain actual acceleration components in the acceleration sensor coordinate system or the speed sensor coordinate system;
  a composition unit for performing a composition operation on the actual acceleration components to obtain acceleration values generated by actual movement of the measurement site; and
  a muscle relaxation calculation unit for calculating the level of muscle relaxation based on the acceleration values identified by subtracting the components of gravity acceleration from the acceleration sampled values;
wherein the gravity acceleration subtraction unit comprises:
  a first subunit for calculating a transition matrix from a reference coordinate system to a kinetic coordinate system according to the acceleration sampled values from the acceleration sensor or the speed sensor and the angular velocity sampled values from the angular velocity sensor at time tk, and obtaining components of the gravity acceleration in the acceleration sensor coordinate system or the speed sensor coordinate system according to components of the gravity acceleration projected in the reference coordinate system and the transition matrix from the reference coordinate system to the kinetic coordinate system, where the time tk is any time after an electrical stimulation, the kinetic coordinate system is the acceleration sensor coordinate system or the speed sensor coordinate system at the time tk, the reference coordinate system is obtained by rotating an initial coordinate system, the initial coordinate system is the acceleration sensor coordinate system or the speed sensor coordinate system at any time before the electrical stimulation and the measurement site staying still.

8. An apparatus for measuring muscle relaxation, comprising:
  a constant-current source for generating stimulative current and through a current output thereof, applying current stimulation on a subject to be detected;
  a response-signal extraction end comprising an acceleration sensor and an angular velocity sensor or comprising a speed sensor and an angular velocity sensor; and
  a processor connected with the constant-current source and communicatively coupled with the response signal extraction end for:
    controlling the constant-current source to generate stimulative current;
    acquiring acceleration sampled values and angular velocity sampled values from motion information outputted by the response-signal extraction end;
    calculating components of gravity acceleration in an acceleration sensor coordinate system or a speed sensor coordinate system according to the acceleration sampled values and the angular velocity sampled values;
    subtracting the components of gravity acceleration from the acceleration sampled values to obtain actual acceleration components in the acceleration sensor coordinate system or the speed sensor coordinate system;
    performing a composition operation on the actual acceleration components to obtain acceleration values generated by actual movement of the measurement site; and
    calculating a level of muscle relaxation according to the acceleration sampled values and the angular velocity sampled values using the acceleration values identified by subtracting the components of gravity acceleration from the acceleration sampled values;
  wherein the processor calculating components of gravity acceleration in an acceleration sensor coordinate system or a speed sensor coordinate system according to the acceleration sampled values and the angular velocity sampled values comprises:
    calculating a transition matrix from a reference coordinate system to a kinetic coordinate system according to the acceleration sampled values from the acceleration sensor or the speed sensor and the angular velocity sampled values from the angular velocity sensor at time tk, and obtaining components of the gravity acceleration in the acceleration sensor coordinate system or the speed sensor coordinate system according to components of the gravity acceleration projected in the reference coordinate system and the transition matrix from the reference coordinate system to the kinetic coordinate system, where the time tk is any time after an electrical stimulation, the kinetic coordinate system is the acceleration sensor coordinate system or the speed sensor coordinate system at the time tk, the reference coordinate system is obtained by rotating an initial coordinate system, the initial coordinate system is the acceleration sensor coordinate system or the speed sensor coordinate system at any time before the electrical stimulation and the measurement site staying still.

9. The apparatus for measuring muscle relaxation according to claim 8, wherein the processor calculating a transition matrix from a reference coordinate system to a kinetic coordinate system according to the acceleration sampled values from the acceleration sensor or the speed sensor and the angular velocity sampled values from the angular velocity sensor at time tk comprises:
  acquiring initial components of gravity acceleration in the initial coordinate system at time t0 from the acceleration sensor or the speed sensor, the time t0 is any time before the electrical stimulation and the measurement site staying still; then calculating a transition matrix from the reference coordinate system to the initial coordinate system at the time t0 based on the initial components of gravity acceleration; calculating a transition matrix from the initial coordinate system to the kinetic coordinate system based on the angular velocity sampled values; and according to the transition matrix from the reference coordinate system to the initial coordinate system and the transition matrix from the initial coordinate system to the kinetic coordinate system, obtaining the transition matrix from the reference coordinate system to the kinetic coordinate system.

10. The apparatus for measuring muscle relaxation according to claim 9, wherein the processor calculating a transition matrix from the reference coordinate system to the initial coordinate system at the time t0 based on the initial components of gravity acceleration comprises:

calculating rotation angles from the initial coordinate system to the reference coordinate system according to the initial components of gravity acceleration, calculating a transition matrix from the initial coordinate system to the reference coordinate system according to the rotation angles and obtaining the transition matrix from the reference coordinate system to the initial coordinate system according to the transition matrix from the initial coordinate system to the reference coordinate system;

the processor calculating a transition matrix from the initial coordinate system to the kinetic coordinate system based on the angular velocity sampled values comprises:

analyzing the angular velocity sampled values to obtain rotation angles along moving direction of individual axis about the measurement site, obtaining vectors of motion state according to the rotation angles along moving direction of individual axis about the measurement site, the vectors of motion state representing motion information about the measurement site when the part is moving after got stimulated, and obtaining a transition matrix from the initial coordinate system to the kinetic coordinate system according to the vectors of motion state.

* * * * *